(12) United States Patent
Weigand

(10) Patent No.: US 7,775,824 B2
(45) Date of Patent: Aug. 17, 2010

(54) CONNECTION DEVICE AND METHOD FOR ITS USE

(75) Inventor: Josef Weigand, Heldenstein (DE)

(73) Assignee: ODU Steckverbindungssysteme GmbH & Co. KG, Muhldorf (DE)

(*) Notice: Subject to any disclaimer, the term of this patent is extended or adjusted under 35 U.S.C. 154(b) by 13 days.

(21) Appl. No.: 11/755,879

(22) Filed: May 31, 2007

(65) Prior Publication Data
US 2007/0285194 A1 Dec. 13, 2007

(30) Foreign Application Priority Data
Jun. 8, 2006 (DE) .................. 10 2006 026 720

(51) Int. Cl.
*H01R 13/627* (2006.01)
(52) U.S. Cl. .................................... 439/357
(58) Field of Classification Search ............ 439/312, 439/320, 314, 357, 369, 474, 909
See application file for complete search history.

(56) References Cited

U.S. PATENT DOCUMENTS

| 4,389,081 A | * | 6/1983 | Gallusser et al. ............ 439/320 |
| 5,427,542 A | * | 6/1995 | Gerow .......................... 439/314 |
| 5,620,330 A | * | 4/1997 | Pizon ........................... 439/350 |
| 5,662,488 A | | 9/1997 | Alden |
| 6,447,323 B1 | * | 9/2002 | Watanabe .................... 439/371 |
| 2005/0136722 A1 | | 6/2005 | Cairns |
| 2005/0177199 A1 | | 8/2005 | Hansen et al. |

FOREIGN PATENT DOCUMENTS

| DE | 44 04 260 A1 | 8/1995 |
| DE | 297 19 217 U1 | 4/1998 |

* cited by examiner

*Primary Examiner*—Phuong K Dinh
(74) *Attorney, Agent, or Firm*—Schwabe, Williamson & Wyatt, P.C.

(57) ABSTRACT

Embodiments of the present invention provide a connection device for the transmission of optical and/or electrical signals, specifically for medical purposes, featuring a cable and a coupling element, which is designed to couple to a matching counterpart on the coupling side. The coupling side exhibits an inner part, having a connecting element for connection to the cable, and an outer part, with the outer part being detachably attached to the inner part. The outer part is capable of being detached from the inner part prior to use of the connection device involving the passage of the connection device through an area of the human body.

14 Claims, 3 Drawing Sheets

CONNECTION DEVICE AND METHOD FOR ITS USE

CROSS REFERENCE TO RELATED APPLICATIONS

The present application claims International Priority under 35 U.S.C. § 119 to co-pending German Patent Application No. 102006026720.6, filed Jun. 8, 2006, entitled "Verbindungsvorrichtung und Verfahren zu deren Einsatz," the entire disclosure of which is hereby incorporated by reference in its entirety.

TECHNICAL FIELD

Embodiments of the present invention relate to a connection device for the transmission of optical and/or electrical signals, specifically for medical purposes, having a cable and a coupling element designed for coupling to a matching counterpart on a coupling side, with the coupling element having an inner part with a connection mechanism for connecting to the cable and an outer part. The invention also relates to a method for establishing an electrical and/or optical connection from an internal area of a body, such as a human body, to the outside.

BACKGROUND

Coupling elements for transmitting optical or electrical signals are well known in the field of medicine. In a specific area of application, they are used to transmit signals from the inside of the body of a patient to the outside of the body of the patient and/or vice versa. This is required, for example, when a medical device, such as an insulin pump, is implanted into the patient's body, and the device needs to be addressed or accessed from the outside, for example for control purposes, and/or needs to be capable of emitting signals to the outside, for example to indicate the status of the device. For this purpose, the cable is passed from the implanted device to the outside of the body through an orifice in the body and the coupling element is coupled to a matching counterpart that, in turn, may be connected to a control device and/or an analytical device.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

DETAILED DESCRIPTION OF EMBODIMENTS OF THE INVENTION

Figure 1:
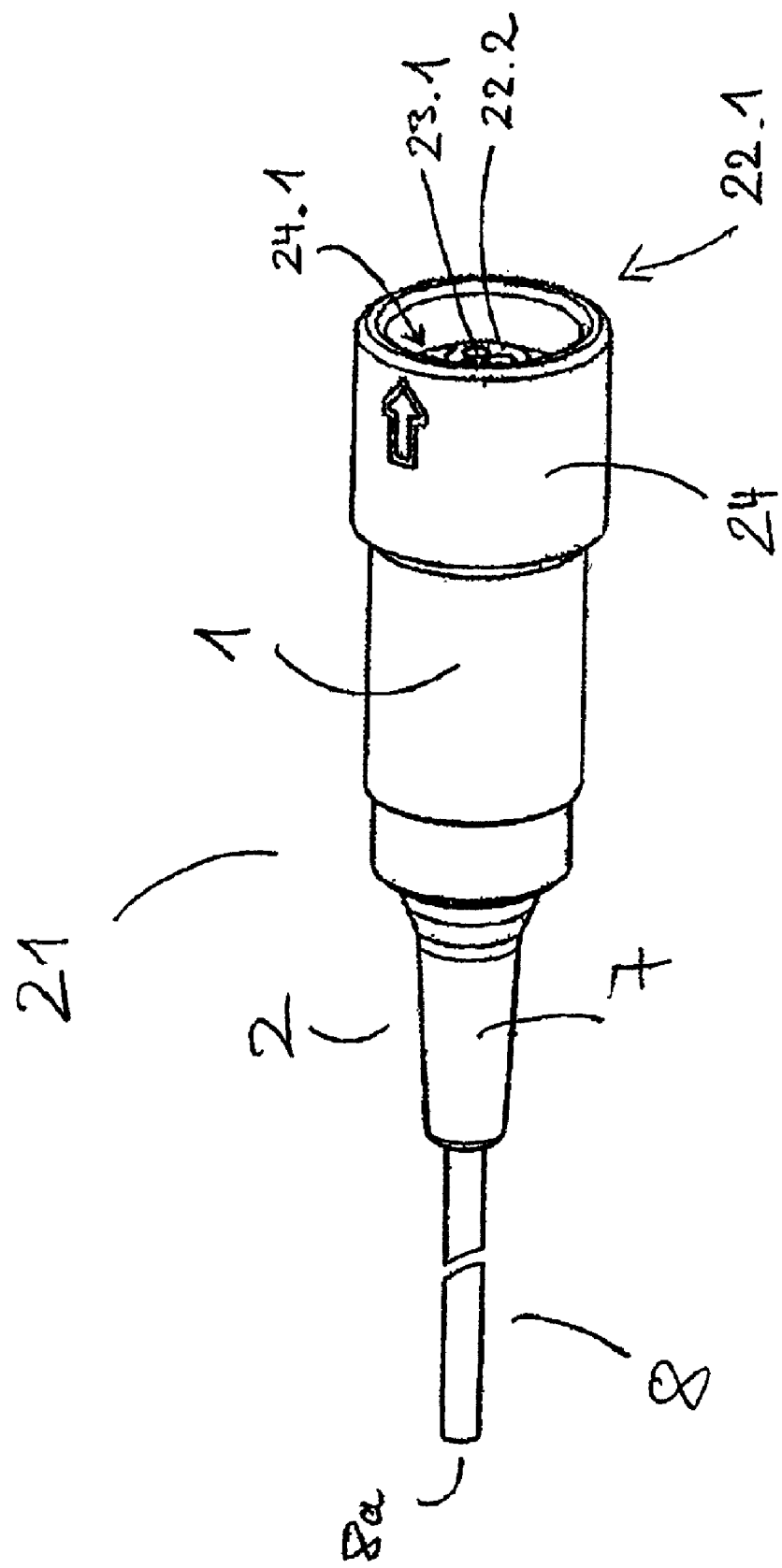
FIG. 1 illustrates a perspective view of an embodiment of a connection device in a connected state in accordance with various embodiments of the present invention.

In the following detailed description, reference is made to the accompanying drawings which form a part hereof, and in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

For the purposes of the description, a phrase in the form "A/B" means A or B. For the purposes of the description, a phrase in the form "A and/or B" means "(A), (B), or (A and B)". For the purposes of the description, a phrase in the form "at least one of A, B, and C" means "(A), (B), (C), (A and B), (A and C), (B and C), or (A, B and C)". For the purposes of the description, a phrase in the form "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

Thus, in an embodiment, there is provided a connection device for the transmission of optical and/or electrical signals, comprising a cable, and a coupling element configured for coupling to a matching counterpart of another device via a coupling end of the coupling element, the coupling element having an inner part with a connecting element for connection to the cable and an outer part, wherein the outer part is detachably coupled to the inner part.

In an embodiment, the cable of the coupling element generally has to be run appropriately. For this purpose, the coupling element may exit the body through an orifice. In an embodiment, the coupling element may be placed such that it enters a body through a first body orifice and exits the body through a second body orifice from the inside of the body to the outside. The body orifices may coincide, but usually they are different openings. This has to do with the fact that a suitable predetermined position may be preferred for the opening for the exit of the coupling element, irrespective of the body area in which the medical device is implanted.

Therefore, in an embodiment, in order to create the electrical and/or optical connection, an invasive procedure is required, in the course of which a passageway into the body of the patient may be created.

Embodiments of the invention are based on the technical problem of providing a coupling element which enables increased minimization of the above-described surgical procedure, in particular the minimization of the dimensions of the passageway.

This problem is solved in accordance with embodiments of the invention by a coupling element of the type described above, in which the outer part is detachably coupled to the inner part, and the inner part is capable of being coupled to the outer part from a side which does not coincide with the coupling side of the outer part.

Therefore, in the coupling element according to an embodiment of the invention, the inner part and the cable may be safely introduced into or led out of the body, since the outer part does not have to be introduced into or led out of the respective orifice(s) along with it, but instead may be attached to the inner part afterwards. In this way, those areas of the body of the patient against which the outer part bumps, pushes and/or on which it pulls when conventional coupling elements are used, are subjected to reduced stress. In an embodiment, it is thus possible, in particular, to make smaller incisions to create the opening(s) than the incisions that were traditionally required in order to make the invasive procedure as minimal as possible.

The coupling element in accordance with an embodiment of the invention therefore exhibits a coupling element which, as compared to traditional coupling elements, has a reduced effective cross-sectional area in relation to the direction of travel of its path to be covered during the insertion/passageway out.

Thus, in embodiments, the terms inner part and outer part should not be understood such that, within the understanding of embodiments of the invention, the outer part has to completely enclose the inner part, but it should be understood that there is a plane relative to which a projection of the coupling element onto the plane given a fixed orientation of the coupling element with respect to a respective projection of the inner part onto the plane given the same orientation is designed such that one dimension of the projection of the coupling element is—in at least one axis lying in the plane and intersecting the projections—larger than a respective dimension of the projection of the inner part.

Since the at least section-wise coupling (e.g. insertion) of the inner part into the outer part proceeds from one side which does not coincide with the coupling side of the outer part, in an embodiment, the outer part does not need to be threaded onto the cable in order to attach it to the inner part. Otherwise, the outer part would have to be passed through the opening(s) of the patient's body.

Thus, in an embodiment, the cable constitutes a kind of topological obstacle for the outer part. Therefore, embodiments of the invention also relate to a connection device for the transmission of optical and/or electrical signals, specifically for medical purposes, via a cable and a coupling element being designed for coupling to a matching counterpart, with the coupling element exhibiting an inner part which may be attached to the cable, as well as an outer part capable of being attached to the inner part in order to create a connected state of the coupling element—starting from a disconnected state of the coupling element, in which the outer part does not enclose the cable in relation to its radial direction—without the outer part having to be penetrated, for this purpose, by an end of the cable that is away from the coupling element or, given that a reversal of motion is effected, an end of the cable that is close to the coupling element.

It is therefore possible, in an embodiment, to attach the outer part to the inner part without having to thread it to the cable. This makes it possible to safely pass the connection device through or into or out of the body in the manner described above.

Advantageously, in an embodiment, the inner part has a longitudinal design so that it has a smaller lateral dimension as compared to its length. In this way, a streamlined form is achieved for the passage through the body.

Such an embodiment may have a lateral dimension in the range of 1 to 12 mm, preferably 2 to 10 mm, specifically 4 to 8 mm. This makes it possible to achieve an even safer use of the connection device, and, in particular, a smaller and thus cosmetically more acceptable exit opening is made possible.

In another embodiment, the ratio of the lateral dimension and the respective dimension of the coupling element expressed as a percentage is in the range of 10% to 85%, for example 30% to 80%, such as 50% to 75%. This enables the safe use of the coupling element, on the one hand, and ensures a high functionality of the coupling element, on the other hand.

Advantageously, in an embodiment, the inner part and/or the coupling element have a circular cross-section making it possible to largely avoid edges or corners presenting a comparatively high risk of injury.

In an embodiment, the outer part envelops the inner part at least in sections in a connected state of the coupling element. Thus, the outer part assumes a protective function for the inner part.

In an embodiment, the inner part is capable of being inserted into, and specifically capable of being retracted from the outer part. This enables the extremely simple and time-saving handling of the connection device.

Advantageously, in an embodiment, a locking mechanism is provided which counteracts the transition from a connected state to a disconnected state of the coupling element, making it possible to largely prevent an undesired and unintended detachment of the inner part and the outer part.

Advantageously, in an embodiment, a guiding device is provided which facilitates the transition from a disconnected state to a connected state of the coupling element, which simplifies the handling of the coupling element.

In an advantageous embodiment of the invention, a positioning device is provided which enables the relative positioning of the inner part with respect to the outer part in the event of a transition from a disconnected state to a connected state of the coupling element. In this way, the inner part may be automatically positioned such that the subsequent coupling to the matching counterpart is possible without any further measures.

In an embodiment of the invention, the outer part does not have a direct connection to a contact side of the inner part designed to create an electrical and/or optical contact with the counterpart, and the inner part is specifically capable of establishing the contact by itself. In this way, the outer part itself is not required for the contact and the functions of contact or protection of the contact are provided separately.

In an advantageous embodiment, the contact side of the inner part has several electrical and/or optical contacts, particularly, in an embodiment, three electrical contacts. In this way, in embodiments, several independent or different signals may be transmitted, on the one hand, and the connection device may thus be particularly adapted to commonly used implantable medical devices.

In an embodiment of the invention, the outer part exhibits a plug device, designed specifically as part of a push-pull mechanism, for the mechanical coupling to the matching counterpart. This makes it possible to ensure a high degree of user-friendliness with respect to the coupling to the matching counterpart.

Advantageously, in an embodiment, the inner part is undetachably connected to the cable. Thus, the connection device features a manageable and small number of individual parts.

Advantageously, in an embodiment, a protective element for its contact side is provided in a section on the coupling side of the inner part, and in particular, the outer part extends further in the direction of the coupling side in its connected state than the coupling-side end of the protective element. Thus, on the one hand, the contact side of the inner part may be protected alone, for example by a kink protection sheath, while, on the other hand, further protection is ensured in the connected state by the outer part.

In an embodiment of the invention, the decoupling of the outer part from the inner part in the direction of the coupling side of the outer part is possible. This ensures simple handling and makes the connection device more user-friendly.

It is furthermore advantageously provided, in an embodiment, that the force required for decoupling is in the range of 0.1 to 20 N, for example 0.8 to 8 N, such as 2.0 to 4.0 N. In this way, a satisfactory connecting force to protect against inadvertent detachment of the inner part from the outer part is ensured, on the one hand, while the user is still able to separate the connection using a comfortable expenditure of energy, on the other hand.

Advantageously, in an embodiment, the connection device is designed such that it is capable of transmitting signals from the body's interior to the outside and vice versa. Thus, this enables not only unilateral but also bilateral communication with an implanted medical device.

Embodiments of the invention also relate to a method for establishing an electrical and/or optical connection from an internal area of a body, such as a human body, to the outside, providing the possibility of the subsequent electrical and/or optical coupling of the connection via a coupling element of a connection device with a matching counterpart, involving the movement of an inner part of the coupling element from the body's interior to the outside, whereby, following the movement and prior to the coupling with the matching counterpart, the inner part and an outer part of the coupling element, capable of being connected with the inner part, are assembled to create a connected state of the coupling element.

The advantages offered by the above-described method as compared to the methods of the state of the art have already been explained above. In summary, it may be said that, according to an embodiment of the invention, only the inner part of the coupling element is moved from the internal area of the human body to the outside, in order to enable a safe surgical procedure, during which the inner part is less protected during the establishment of the connection than it is in conventional methods. But, this reduced protection is of no importance because the protection is reduced only during the establishment of the connection and not during the operation.

In accordance with the above description, the method described above may comprise the further upstream operations of decoupling of the outer part from the inner part and the introduction of solely the inner part into the internal area of the body from the outside. Accordingly, in an embodiment, a connection device designed for such a method is also provided.

In addition, in accordance with the above-stated explanations, an embodiment of the invention provides for the use of a coupling element, having an outer part that is detachable from its inner part, for the introduction of the inner part into the interior of the patient's body through a first orifice and for the exiting of the inner part from the interior of the patient's body through a second orifice, with the coupling element being capable of being put into a disconnected state from the connected state for the introduction and/or the exit.

FIG. 1 shows an embodiment of a connection device in accordance with an embodiment of the invention with a coupling element 21 of the connection device being presented in a connected state. FIG. 1 shows outer part 1 of coupling element 21, and an arrow on end area 24, which is away from the cable, of outer portion 1 that points in the direction of coupling side 22.1 of outer part 1. In the connected state, an inner part 2 of coupling element 21 is arranged in sections in the interior of outer part 1 or enveloped by outer part 1.

With respect to inner part 2, FIG. 1 shows—toward coupling side 22.1 of outer part 1—a coupling-side end 22.2 of inner part 2 with an output of an electrical contact 23.1 of contact side 23 (see FIG. 2) of inner part 2, as well as a cable-side end area of inner part 2, which, in an embodiment, is designed as kink protection sheath 7, providing protection against kinking in the cable connection area. Furthermore, FIG. 1 shows a cable 8, capable of transmitting electrical signals in an embodiment, with its end 8b (see FIG. 2) that is close to coupling element 21 being covered in FIG. 1 by inner part 2 and with its end 8a, which is away from the coupling element, being shown disconnected. In embodiments, cable 8 may be longer than it is shown in FIG. 1.

As is clearly discernible in FIG. 1, both coupling element 21 and inner part 2 have a longitudinal design, and both exhibit a circular cross-section, which, however, may be differently sized in the longitudinal direction. Thus, for example, coupling-side area 24 of outer part 1 is provided with the largest diameter or the largest lateral dimension, for, within area 24, space is being reserved for coupling of a matching counterpart of the connection device.

Figure 2:
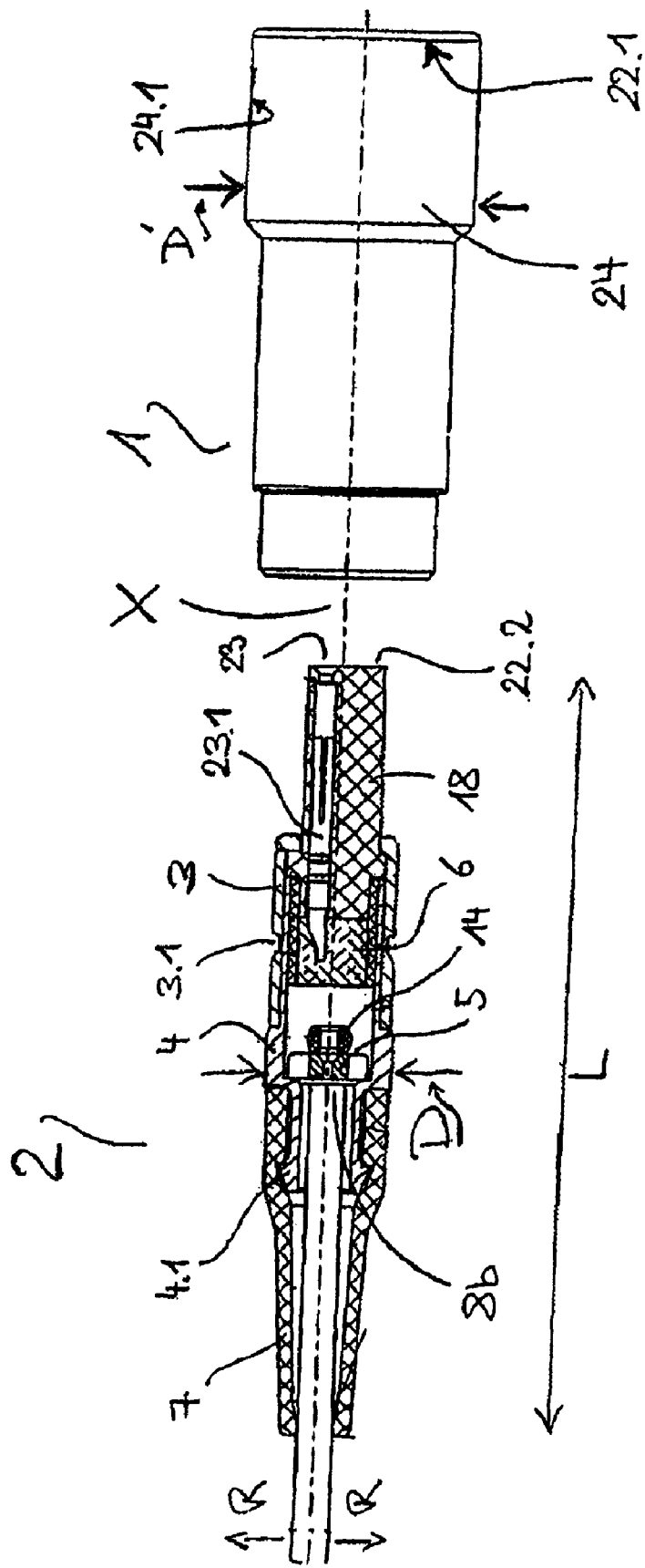
FIG. 2 illustrates a longitudinal section of an inner part of the coupling element of the connection device shown in FIG. 1, but in a disconnected state, as well as an exterior view of its outer part.

Coupling element 21 may be moved from the connected state shown in FIG. 1 to the disconnected state shown in FIG. 2, simply by detaching outer part 1 from inner part 2 in the direction of the arrow, i.e. in the direction of coupling side 22.1 of outer part 1. Vice versa, coupling element 21 may be moved back, in an embodiment, from the disconnected state shown in FIG. 2 to the connected state shown in FIG. 1, by inserting inner part 2 from the opposite side of coupling side 22.1 of outer part 1 in the direction of the arrow into outer part 1. Thus, inner part 2 is not coupled to or inserted into outer part 1 from a side coinciding with coupling side 22.1 of outer part 1.

FIG. 2 shows a disconnected state of coupling element 21, in which outer part 1 does not enclose cable 8 relative to its radial direction. Outer part 1 may be coupled to inner part 2 in the opposite direction of the arrow shown in FIG. 1, without it having to be threaded first to cable 8. This means that there is no need for outer part 1 to be penetrated by end 8a, which is away from coupling element 21, of cable 8 (threading from the side of the distant cable end) or to be penetrated by end 8b, which is close to coupling element 21, of cable 8, given that a reversal of motion is effected.

In addition to outer part 1, FIG. 2 also shows inner part 2 in a longitudinal view. One can see that a main body of inner part 2 is comprised of a front shell 3 and a rear shell 4. Rear shell 4 tapers off to form the cable-side end and finally, in an embodiment, forms a ring-shaped protrusion 4.1 in its end area. Ring-shaped protrusion 4.1 ensures that kink protection sheath 7 is not detachable from inner part 2 following the assembly of inner part 2 so that kink protection sheath 7 is not subject to the risk of loss as a further individual part. Cable 8 is attached through a ring 5 and a ball 14 via its end 8b, which is close to coupling element 21, via a connecting element within rear shell 4.

In an embodiment, the pins of cable 8 are connected with contact side 23 of inner part 2, with only an electrical contact 23.1 of contact side 23 being visible in FIG. 2.

Figure 3:
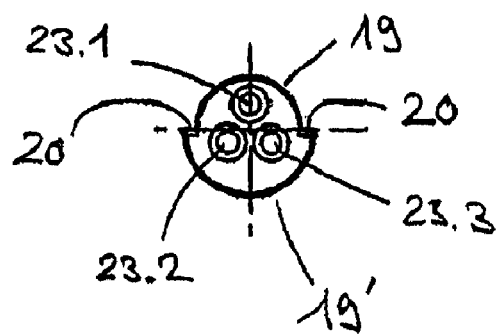
FIG. 3 illustrates a front view of a coupling end area of the inner part shown in FIG. 2.

At its end that is away from cable 8, front shell 3 has an opening, from which a protective element 18 extends in the direction of coupling side 22, which protectively encloses three electrical contacts 23.1, 23.2 and 23.3, as can be seen in a front view in FIG. 3. The interior space of inner part 2 between the connecting mechanism and protective element 18 exhibits a grouted sheath 6. In an embodiment, outer part 1 is not involved in the electrical contact between inner part 2 and the counterpart.

Kink protection sheath 7 is preferably made from a hard rubber or rubber-like material. Front shell 3 and rear shell 4 are preferably made from a solid material such as metal, and protective element 18 is preferably made from a solid material, which is, however, easily moldable in the manufacturing process, such as hard plastic.

As is clearly shown in FIG. 2, inner part 2 may be inserted into outer part 1 for part of its length L along a central axis X. It is also clearly shown that the diameter or the lateral dimension D of inner part 2 is clearly smaller than the corresponding (largest) lateral dimension D' of outer part 1, which at the same time represents the largest lateral dimension of coupling element 21. In an embodiment, the diameter D of inner part 2 is approximately 7 mm and the ratio of the diameters or the lateral dimensions D/D' is approximately 57%. Coupling element 21 is therefore dimensioned such that inner part 2 exhibits a cross-sectional area related to the axis X, which, in an embodiment, amounts to only ⅓ of the respective cross-sectional area of coupling element 21 in the disconnected state. For this reason, the connection device in accordance with an embodiment of the invention may be used in a considerably safer manner than conventional connection devices having coupling elements of comparable dimensions.

A ring-shaped notch 3.1 of front shell 3 of inner part 2 is part of the locking mechanism which locks inner part 2 into outer part 1. This is shown more clearly in FIG. 4, which shows, in addition to inner part 2, an area of outer part 1 that is not visible in FIG. 1 and FIG. 2. This concerns a coupling nut 12, which is attached within a center section of outer part 1. Coupling nut 12 is designed such that it pushes an annular flange 11.1 protruding to the inside into ring-shaped notch 3.1. In this way, together with ring-shaped notch 3.1, annular flange 11.1 forms a locking mechanism that protects coupling element 21 from inadvertent transition to the disconnected state.

In an embodiment, the disengagement of locking mechanism requires a force of approximately 3 N.

Figure 4:
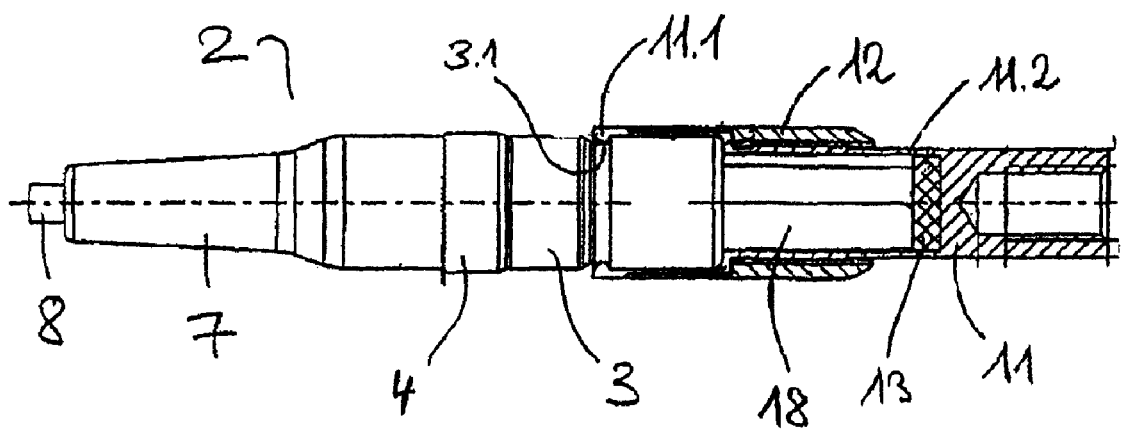
FIG. 4 illustrates a partially cut-away partial view of the connection device shown in FIG. 1, which is coupled with a matching counterpart, with one portion of the outer part and one portion of the counterpart being represented in a longitudinal sectional view.

FIG. 4 also shows a portion of a matching counterpart of the connection device, which has the shape of a claw sleeve 11. Claw sleeve 11 exhibits a flat gasket 13 facing coupling-side end 22.2 of protective element 18 of inner part 2. FIG. 4 does not show the three electric contact pins that extend from claw sleeve 11 in the direction of inner part 2 of coupling element 21 and that are designed to be inserted into the reception areas of electrical contacts 23.1, 23.2, 23.3 of contact side 23 of inner part 2.

FIG. 3 shows a front view of protective element 18 of inner part 2, with electrical contacts 23.1, 23.2, 23.3 appearing as annular rings which define the areas for the reception of the electrical contact pins of the counterpart. FIG. 3 also shows that protective element 18 has an essentially circular cross-section. More precisely, the cross-section of protective element 18 is comprised of two semi-circular areas with different radii, so that protective element 18 exhibits differently shaped partial cylinder surface areas 19, 19', which are connected to each other via edge areas 20 along the central axis X, which is vertical to the paper plane in FIG. 3. The opening area of front shell 3, from which protective element 18 extends, has the same form and size as the cross-section of protective element 18 shown in FIG. 3. A distant end area of coupling nut 12 (on the opposite side of annular flange 11.1) also features a slightly flexible flange area protruding to the inside, which leaves an opening of exactly the shape corresponding to the cross-section shown in FIG. 3. This, however, is not shown in FIG. 4.

The above-described corresponding form of the cross-section of protective element 18 constitutes a guiding device by means of which protective element 18 of inner part 2 and, consequently, inner part 2 may be easily inserted into outer part 1 of coupling element 21. In addition, longitudinal edges 20 between areas 19 of protective element 18 serve as a positioning device which establishes the precise position of electrical contacts 23.1, 23.2, 23.3 relative to outer part 1 of coupling element 21. Given a respective design of claw area 11.2 of claw sleeve 11 of the counterpart, the contact pins of the counterpart are automatically positioned correctly in order to be automatically inserted correctly into the reception areas of electrical contacts 23.1, 23.2 and 23.3 when claw sleeve 11 is coupled to contact side 23 of inner part 2.

FIG. 1 further shows, suggestively, that outer part 1 exhibits a ring-shaped notch 24.1 on the inner side of its coupling-side area 24 (the area with the largest lateral dimension D'). Ring-shaped notch 24.1 constitutes a plug device for mechanical coupling to the matching counterpart. It may be designed, for example, as part of a push-pull mechanism and therefore allows the same mechanical coupling quality of coupling element 21 that is displayed by conventional coupling elements, i.e. the possibility, provided in accordance with an embodiment of the invention, of disconnecting outer part 1 from inner part 2 of coupling element 21 does not affect its quality of coupling to the matching counterpart.

The embodiments of the present invention shown in FIGS. 1, 2, 3, and 4 are intended to serve as illustrations of embodiments of the invention protected in the claims and should not be considered as limiting its protection. Instead, the features of the invention disclosed in the above description as well as the claims may be essential both individually and in any combination for the implementation of the invention in its various embodiments.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A connection device for the transmission of optical and/or electrical signals, comprising:
    a cable; and a coupling element configured for coupling to the cable and to a matching counterpart of another device via a coupling end of the coupling element, said coupling element having an inner part with a connecting element for connection to the cable and an outer part for coupling to the matching counterpart, wherein the outer part is detachably coupled to the inner part, wherein the outer part comprises a first coupling end for coupling to the matching counterpart and a second end through which the inner part is axially insertable along an insertion axis for its detachable coupling to the outer part, said coupling element comprising a positioning device that enables the insertion of the inner part into the outer part only in a given relative positioning of the inner part relative to the outer part in a plane orthogonal to the insertion axis and that prevents rotation between the inner part and the outer part when the inner part is inserted into the outer part.

2. The connection device of claim 1, wherein the cable has a first end proximal to the coupling element and a second end distal to the coupling element, wherein the outer part is capable of being coupled to and decoupled from the inner part with only the proximal end of the cable penetrating the second end of the outer part.

3. The connection device of claim 1, wherein the inner part is connected to the cable.

4. The connection device of claim 1, wherein the inner part has a longitudinal shape having a lateral dimension and a length, wherein the lateral dimension is smaller than the length.

5. The connection device of claim 4, wherein the lateral dimension is in the range of 4 to 8 mm.

6. The connection device of claim 4, wherein the ratio of the lateral dimension of the inner part to a corresponding lateral dimension of the outer part expressed as a percentage is from 50% to 75%.

7. The connection device of claim 1, wherein at least one of the inner part and the coupling element have a circular cross-section.

8. The connection device of claim 1, wherein the outer part encloses at least a portion of the inner part when the outer part is coupled to the inner part.

9. The connection device of claim 1, further comprising a locking flange on the outer part that interacts with a corresponding annular notch on the inner part.

10. The connection device of claim 1, wherein said positioning device comprises a guiding portion on the inner part.

11. The connection device of claim 1, wherein the inner part has a contact end for optical and/or electrical contact with a corresponding contact end on the matching counterpart.

12. The connection device of claim 11, wherein the contact end of the inner part has one or more electrical and/or optical contacts.

13. The connection device of claim 12, wherein the inner part has a protective element that at least partially encloses the one or more electrical and/or optical contacts.

14. The connection device of claim 1, wherein the outer part has an annular notch for mechanical coupling to the matching counterpart.

* * * * *